(12) United States Patent
Xu et al.

(10) Patent No.: US 10,993,051 B2
(45) Date of Patent: Apr. 27, 2021

(54) HEARING DEVICE WITH NEURAL NETWORK-BASED MICROPHONE SIGNAL PROCESSING

(71) Applicant: Starkey Laboratories, Inc., Eden Prairie, MN (US)

(72) Inventors: Buye Xu, Minnetonka, MN (US); Ivo Merks, Eden Prairie, MN (US); Frederic Philippe Denis Mustiere, Chaska, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 16/662,931

(22) Filed: Oct. 24, 2019

(65) Prior Publication Data

US 2020/0059740 A1 Feb. 20, 2020

Related U.S. Application Data

(63) Continuation of application No. 15/092,489, filed on Apr. 6, 2016, now Pat. No. 10,492,008.

(51) Int. Cl.
*H04R 25/00* (2006.01)
*H04R 1/10* (2006.01)
(Continued)

(52) U.S. Cl.
CPC ....... *H04R 25/507* (2013.01); *A61N 1/36036* (2017.08); *H04R 25/407* (2013.01); *H04R 25/552* (2013.01); *H04R 1/1008* (2013.01); *H04R 5/033* (2013.01); *H04R 25/554* (2013.01); *H04R 2225/43* (2013.01); *H04R 2460/13* (2013.01)

(58) Field of Classification Search
CPC .. H04R 25/507; H04R 25/552; H04R 1/1008; H04R 5/033; H04R 2225/43; H04R 2460/13
See application file for complete search history.

(56) References Cited

U.S. PATENT DOCUMENTS

| | | | |
|---|---|---|---|
| 6,539,096 B1 | 3/2003 | Sigwanz et al. | |
| 7,259,520 B2 * | 8/2007 | Fujiwara | B82Y 10/00 313/504 |

(Continued)

FOREIGN PATENT DOCUMENTS

| | | | |
|---|---|---|---|
| WO | WO-0197558 A2 * | 12/2001 | ........... H04R 25/552 |
| WO | WO-0197558 A2 | 12/2001 | |

OTHER PUBLICATIONS

"U.S. Appl. No. 15/092,489, Advisory Action dated Feb. 2, 2018", 6 pgs.

(Continued)

*Primary Examiner* — Sunita Joshi
(74) *Attorney, Agent, or Firm* — Schwegman Lundberg & Woessner, P.A.

(57) ABSTRACT

A hearing system performs nonlinear processing of signals received from a plurality of microphones using a neural network to enhance a target signal in a noisy environment. In various embodiments, the neural network can be trained to improve a signal-to-noise ratio without causing substantial distortion of the target signal. An example of the target sound includes speech, and the neural network is used to improve speech intelligibility.

27 Claims, 7 Drawing Sheets

(51) Int. Cl.
*H04R 5/033* (2006.01)
*A61N 1/36* (2006.01)

(56) References Cited

U.S. PATENT DOCUMENTS

| | | | |
|---|---|---|---|
| 7,324,649 B1 | 1/2008 | Knapp et al. | |
| 7,359,520 B2* | 4/2008 | Brennan | H04R 3/005 381/122 |
| 7,742,612 B2 | 6/2010 | Frohlich et al. | |
| 7,929,721 B2 | 4/2011 | Knapp et al. | |
| 2003/0063759 A1* | 4/2003 | Brennan | H04R 3/005 381/92 |
| 2008/0212810 A1* | 9/2008 | Pedersen | H04R 25/407 381/312 |
| 2010/0008526 A1* | 1/2010 | De Vries | H04R 25/70 381/314 |
| 2010/0027820 A1* | 2/2010 | Kates | H04R 25/505 381/312 |
| 2013/0195296 A1* | 8/2013 | Merks | H04R 25/402 381/313 |
| 2015/0112672 A1* | 4/2015 | Giacobello | G10L 21/0208 704/233 |
| 2017/0295439 A1 | 10/2017 | Xu et al. | |

OTHER PUBLICATIONS

"U.S. Appl. No. 15/092,489, Advisory Action dated Oct. 23, 2018", 3 pgs.
"U.S. Appl. No. 15/092,489, Corrected Notice of Allowability dated Sep. 24, 2019", 3 pgs.
"U.S. Appl. No. 15/092,489, Examiner Interview Summary dated Feb. 2, 2018", 1 pg.
"U.S. Appl. No. 15/092,489, Final Office Action dated Jul. 30, 2018", 30 pgs.
"U.S. Appl. No. 15/092,489, Final Office Action dated Nov. 13, 2017", 25 pgs.
"U.S. Appl. No. 15/092,489, Non Final Office Action dated Feb. 28, 2018", 30 pgs.
"U.S. Appl. No. 15/092,489, Non Final Office Action dated Apr. 3, 2019", 20 pgs.
"U.S. Appl. No. 15/092,489, Non Final Office Action dated Jun. 2, 2017", 24 pgs.
"U.S. Appl. No. 15/092,489, Notice of Allowance dated Jul. 26, 2019", 10 pgs.
"U.S. Appl. No. 15/092,489, Response filed Jan. 12, 2018 to Final Office Action dated Nov. 13, 2017", 12 pgs.
"U.S. Appl. No. 15/092,489, Response filed Feb. 13, 2018 to Advisory Action dated Feb. 2, 2018", 12 pgs.
"U.S. Appl. No. 15/092,489, Response Filed May 25, 2018 to Non Final Office Action dated Feb. 28, 2018", 13 pgs.
"U.S. Appl. No. 15/092,489, Response filed Sep. 5, 2017 to Non Final Office Action dated Jun. 2, 2017", 10 pgs.
"U.S. Appl. No. 15/092,489, Response Filed Oct. 1, 2018 to Final Office Action dated Jul. 30, 2018", 12 pgs.
"U.S. Appl. No. 15/092,489, Response filed Jul. 1, 2019 to Non-Final Office Action dated Apr. 3, 2019", 11 pgs.
"U.S. Appl. No. 15/092,489, Supplemental Amendment and Response filed Oct. 3018 to Advisory Action dated Oct. 23, 2018", 11 pgs.
"European Application Serial No. 17165255.5, Communication Pursuant to Article 94(3) EPC dated Jul. 17, 2018", 5 pgs.
"European Application Serial No. 17165255.5, Extended European Search Report dated Jul. 31, 2017", 8 pgs.
"European Application Serial No. 17165255.5, Response filed Apr. 6, 2018 to Extended European Search Report dated Jul. 31, 2017", 45 pgs.
Anitha, M., et al., "Neural fuzzy Inference Based Robust Adaptive Beamforming", IJETAE 2013 vol. 3, Issue 11, (Nov. 2013), 641-648.
Castaldi, G., et al., "Evaluation of a neural-network-based adaptive beamforming scheme with magnitude-only constraints", Progress in Electromagnetics Research B, vol. 11, (2009), 1-14.
Li, Y., "Methods for the blind signal separation problem", Neural Networks and Signal Processing, 2003, (2003).
Li, Yan, et al., "Comparison of Blind Source Separation Algorithms", Advances in Neural Networks and Applications, WSES, (2000), 6 pgs.
Pertila, Pasi, et al., "Microphone Array Post-Filtering Using Supervised Machine Learning for Speech Enhancement", Interspeech 2014, (2014), 5 pgs.
Zooghby, A. H., et al., "A neural-network-based linearly constrained minimum variance beamformer", Microwave and optical technology letters, vol. 21, No. 6, (Jun. 20, 1999), 451-455.

* cited by examiner

HEARING DEVICE WITH NEURAL NETWORK-BASED MICROPHONE SIGNAL PROCESSING

CROSS-REFERENCE TO RELATED APPLICATION

This application is a continuation of U.S. patent application Ser. No. 15/092,489, filed Apr. 6, 2016, which is incorporated by reference herein in its entirety.

TECHNICAL FIELD

This document relates generally to hearing systems and more particularly to a system for processing microphone signals using a neural network.

BACKGROUND

Hearing devices provide sound for the wearer. Some examples of hearing devices are headsets, hearing aids, speakers, cochlear implants, bone conduction devices, and personal listening devices. Hearing aids provide amplification to compensate for hearing loss by transmitting amplified sounds to their ear canals. Damage to outer hair cells in a patient's cochlea results in loss of frequency resolution in the patient's auditory perception. As this condition develops, it becomes difficult for the patient to distinguish target sound, such as speech, from environmental noise. Simple amplification does not address such difficulty. Thus, there is a need to help such a patient in listening to target sounds, such as speech, in a noisy environment.

SUMMARY

According to the present disclosure, a hearing system performs nonlinear processing of signals received from a plurality of microphones using a neural network to enhance a target signal in a noisy environment. In various embodiments, the neural network can be trained to improve a signal-to-noise ratio without causing substantial distortion of the target signal. An example of the target sound includes speech, and the neural network is used to improve speech intelligibility.

In an exemplary embodiment, a hearing system includes a plurality of microphones, a control circuit, and a receiver (speaker). The microphones receive input sounds including a target sound and produce a plurality microphone signals including the target sound. The control circuit produces an output signal using the plurality of microphone signals. The control circuit includes a neural network and controls a directionality of the plurality of microphones by processing the plurality of microphone signals using a nonlinear signal processing algorithm that is based on the neural network. The receiver produces an output sound using the output signal.

In an exemplary embodiment, a hearing system includes a pair of left and right hearing aids configured to be worn by a wear and communicatively coupled to each other. The left and right hearing aids each include a microphone, a control circuit, and a receiver. The microphone receives input sounds including a target sound and produces a microphone signal including the target sound. The control circuit produces an output signal using the microphone signals produced by microphones of the left and right hearing aids. The control circuit includes a neural network and controls a directionality of the microphones of the left and right hearing aids using a nonlinear signal processing algorithm that is based on the neural network. The receiver produces an output sound using the output signal.

In an exemplary embodiment, a method for operating a hearing system to enhance a target sound is provided. Microphone signals including a target sound are received from a plurality of microphones of the hearing system. The microphone signals are processed, using a neural network-based non-linear signal processing algorithm, to control a directionality of the plurality of microphones and produce an output signal. An output sound is produced based on the output signal using a receiver of the hearing system.

This summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, a hearing system that performs neural network based processing of microphone signals to enhance target sounds for better listening, such as improving speech intelligibility in a noisy environment. Though speech intelligibility is discussed as a specific example in this document, the present subject matter can be applied in various hearing devices for enhancing target sounds of any type (e.g., speech or music) in a noisy signal (e.g., babble noise or machine noise). Such devices include, among other things, hearing assistance devices, such as headsets, hearing aids, speakers, cochlear implants, bone conduction devices, and personal listening devices.

Bilateral directional microphones and binaural beam-forming have been used in hearing assistance devices for processing signals including speeches with noisy background, with limited improvement in signal-to-noise ratio (SNR). The present subject matter can use a neural network based binaural algorithm that can achieve performance exceeding the theoretical upper limit provided by a directional microphone or a binaural beamformer in processing microphone signals for a hearing assistance system. The neural network based binaural algorithm is a nonlinear signal processing algorithm that can exceed the theoretical limit achievable by the existing linear algorithms in processing binaural microphone signals. Training of this neural network is highly flexible and may take into account various measures as cost functions. Specific neural network structure and training strategy have been designed and tested to achieve a desirable balance between sound quality and SNR improvement. In various embodiments, the neural network based nonlinear signal processing algorithm can introduce controlled nonlinearity to the signals such that the SNR can be greatly improved while the sound quality is not substantially compromised.

Figure 1:
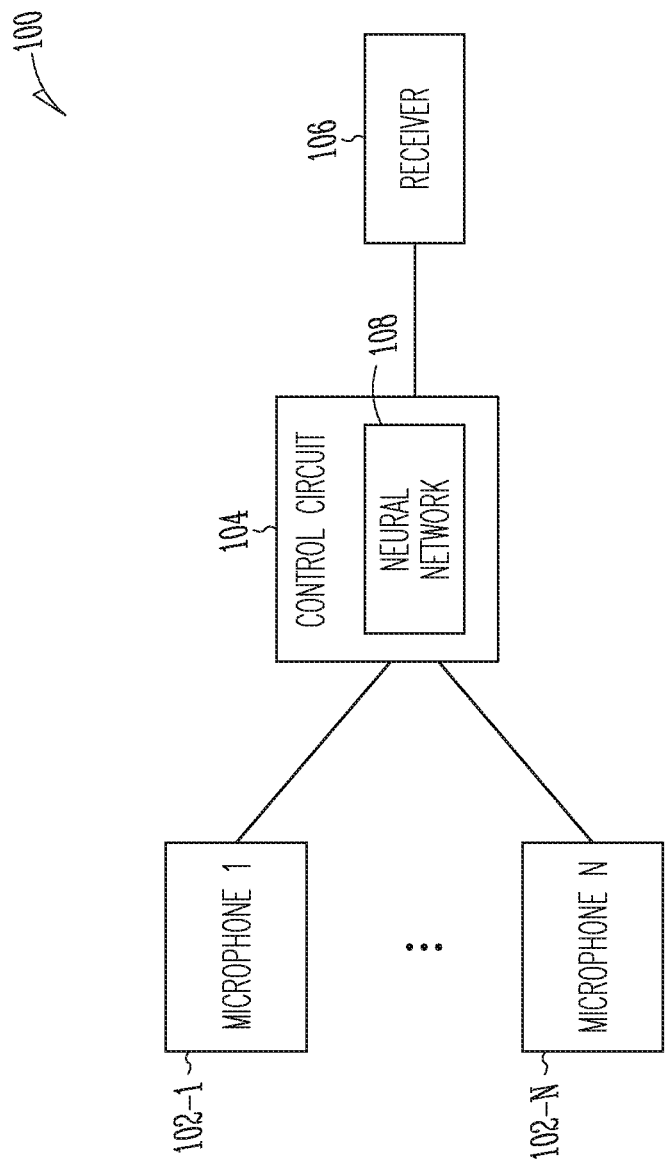
FIG. 1 is a block diagram illustrating an exemplary embodiment of a hearing system using a neural network for processing microphone signals.

FIG. 1 is a block diagram illustrating an exemplary embodiment of a hearing system 100 that uses a neural network for processing microphone signals. System 100 includes a plurality of microphones 1-N (102-1 to 102-N), a control circuit 104, and a receiver (speaker) 106.

Microphones 102 produce a plurality of microphone signals including speech. In one embodiment, microphones 102 are two microphones (N=2). In various embodiments, microphones 102 can include two or more microphones. Microphones 102 are each communicatively coupled to control circuit 104 via a wired or wireless link. Control circuit 104 processes the plurality of microphone signals to produce an output signal. Receiver 106 produces an output sound using the output signal and transmits the output sound to a listener.

Control circuit 104 can include a neural network 108 and control directionality of microphones 102 using the plurality of microphone signals by executing a neural network based signal processing algorithm. In various embodiments, the neural network based signal processing algorithm can include a nonlinear signal processing algorithm. In various embodiments, neural network 108 can be trained to control the directionality of microphones 102 by processing the plurality of microphone signals to achieve a desirable balance between the SNR (with the clean speech being the target signal) and the distortion of the speech, as further discussed below, with reference to FIGS. 3-9. In various embodiments, control circuit 104 can precondition the plurality of microphone signals before processing it using neural network 108, such as by amplifying and/or filtering each of the microphone signals as needed. In various embodiments, control circuit 104 can process the output of neural network 108 to produce right output signal as needed.

In various embodiments, system 100 can be implemented entirely or partially in hearing aids. For example, microphones 102 can include one or more microphones in the hearing aids, one or more ad-hoc microphone arrays, and one or more remote microphones that are external to but communicatively coupled to the hearing aids. Control circuit 104 can be implemented in one or more processors of the hearing aids and/or one or more processors in an external device communicatively coupled to the hearing aids. One example of such an external device includes a cellphone installed with an application implementing portions of control circuit 104. In addition to or in place of receiver 106 for transmitting the output to the listener being a hearing aid wearer, the output can be delivered to another person or device as needed, such as a user other than the hearing aid wearer or a speech recognizer.

Figure 2:
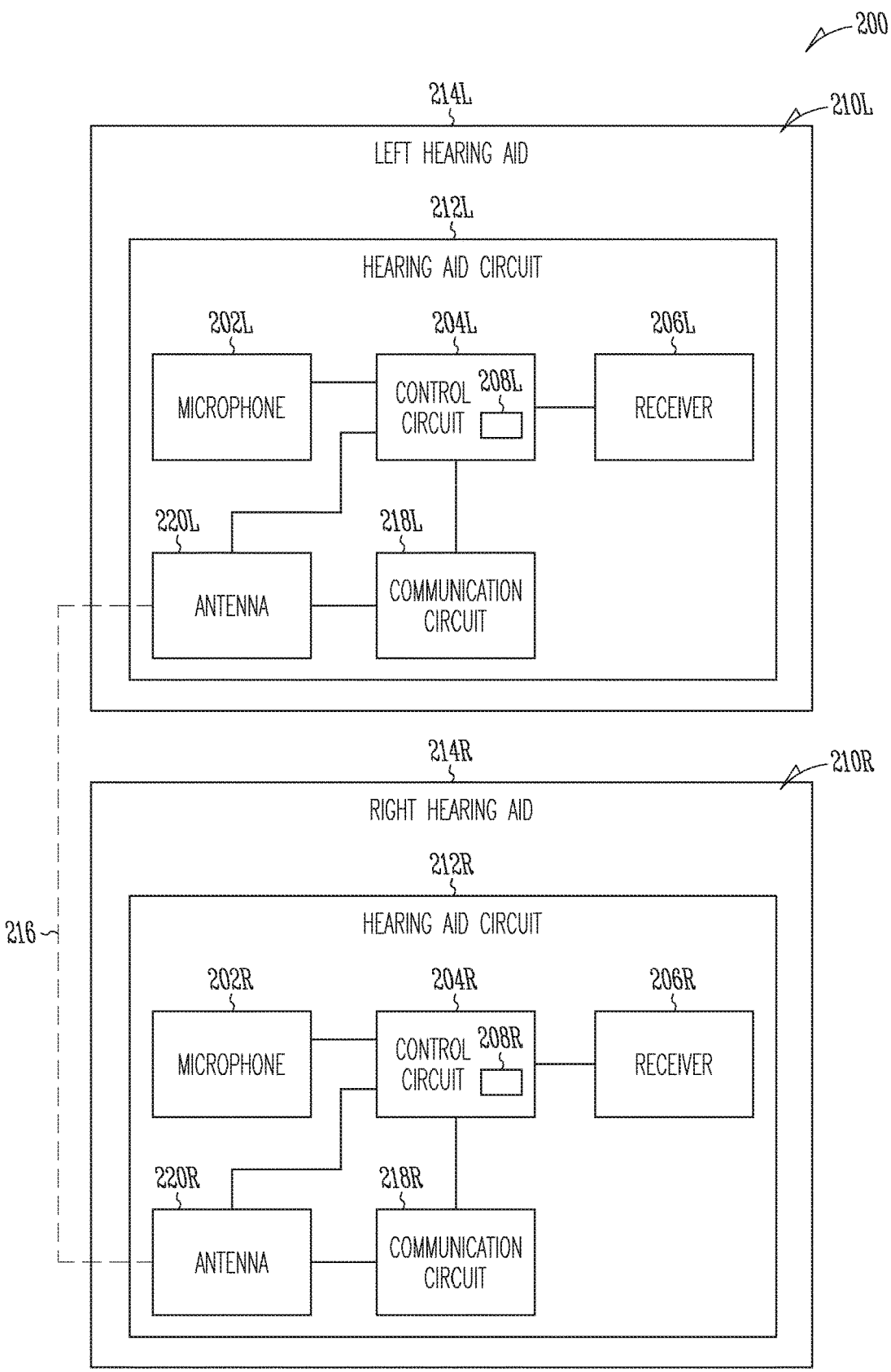
FIG. 2 is a block diagram illustrating an exemplary embodiment of a pair of hearing aids including the neural network.

FIG. 2 is a block diagram illustrating an exemplary embodiment of a hearing system 200, which represents an exemplary embodiment of system 100 with a pair of hearing aids each including a neural network. System 200 includes a left hearing aid 210L and a right hearing aid 210R communicatively coupled to each other via a wireless binaural link 216.

Left hearing aid 210L can be configured to be worn in or about the left ear of a hearing aid wearer and includes a hearing aid circuit 212L and a shell 214L that houses hearing aid circuit 212L. Examples of shell 214L include, but are not limited to, a housing for a BTE, ITE, ITC, RIC, CIC, RITE or deep insertion types of hearing aids for use with the left ear. Hearing aid circuit 212L includes a microphone 202L, an antenna 220L, a communication circuit 218L, a control circuit 204L, and a receiver (speaker) 206L. Microphone 202L receives sounds from the environment of the hearing aid wearer and produces a left microphone signal representing the received sounds. Communication circuit 218L performs wireless communication including ear-to-ear communication with right hearing aid 210R using antenna 220L via binaural link 216. Control circuit 204L processes the left microphone signal and a right microphone signal received by communication circuit 218L to produce a left output signal. Receiver 206L produces a left sound using the left output signal and transmits the left sound to the left ear of the hearing aid wearer.

Right hearing aid 210R can be configured to be worn in or about the right ear of the hearing aid wearer and includes a hearing aid circuit 212R and a shell 214R that houses hearing aid circuit 212R. Examples of shell 214R include, but are not limited to, housing for a BTE, ITE, ITC, MC, CIC, RITE or deep insertion types of hearing aids for use with the right ear. Hearing aid circuit 212R includes a microphone 202R, an antenna 220R, a communication circuit 218R, a control circuit 204R, and a receiver (speaker) 206R. Microphone 202R receives sounds from the environment of the wearer and produces a right microphone signal representing the received sounds. Communication circuit 218R performs wireless communication including ear-to-ear communication with left hearing aid 210L using antenna 220R via binaural link 216. Control circuit 204R processes the right microphone signal and the left microphone signal received by communication circuit 218R to produce a right output signal. Receiver 206L produces a right sound using the right output signal and transmits the right sound to the left ear of the hearing aid user.

Control circuit 204L represents an exemplary embodiment of control circuit 104 and includes a neural network 208L. Control circuit 204R also represents an exemplary embodiment of control circuit 104 and includes a neural network 208R. Examples of neural networks 208L and 208R include neural network 108 including its various embodiments as discussed in this document. In various embodiments, control circuit 204L can precondition the left microphone signal before processing it using neural network 208L and/or processes the output of neural network 208L to produce the left output signal as needed. Control circuit 204R preconditions the right microphone signal before processing it using neural network 208R and/or processes the output of neural network 208R to produce the right output signal, as needed.

Figure 3:
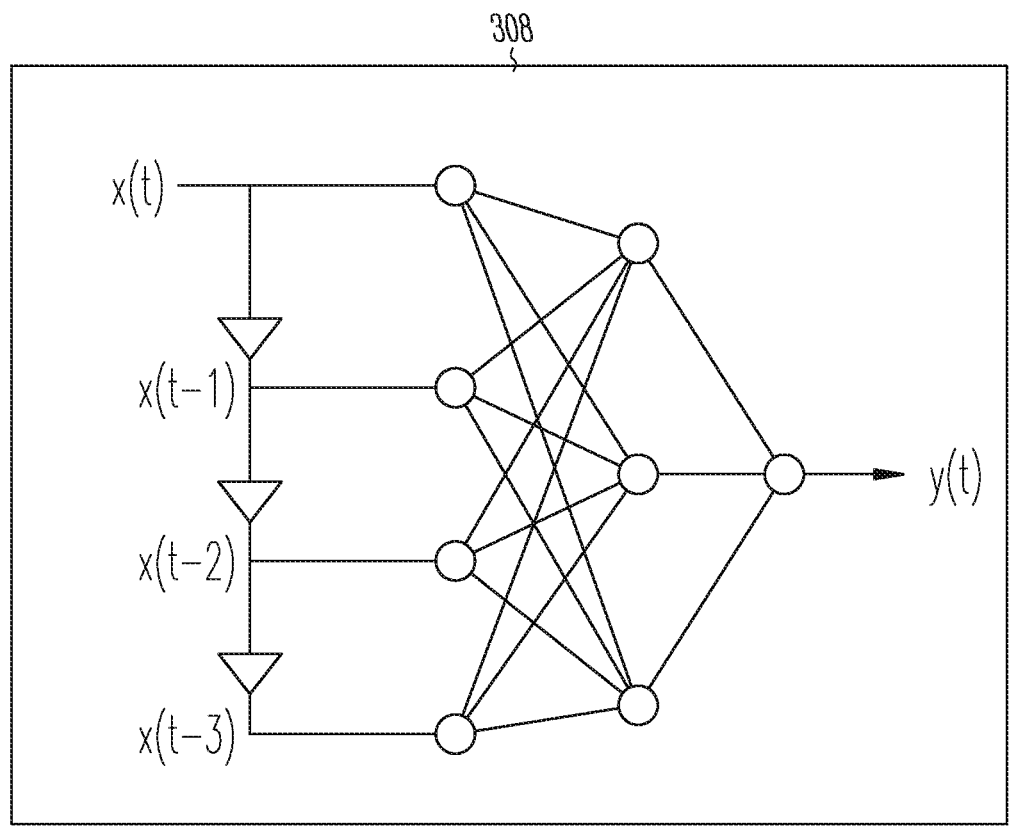
FIG. 3 is an illustration of an exemplary embodiment of a neural network.

FIG. 3 is an illustration of an exemplary embodiment of a neural network 308. The illustrated embodiment is an example of a time domain neural network structure that takes delayed time domain signals (x(t), x(t-1), x(t-2), x(t-3), . . . ) as inputs and generate y(t) as output. This type of structure can be easily modified to process multiple input signals and generate multiple output signals. Neural network 308 can be trained to process microphone signals such as the signals output from microphones 102 or microphones 202L and 202R, and provide an output signal with improved SNR for improved speech intelligibility. In an exemplary embodiment, neural network 308 is a fixed neural network that remains unchanged after training. In another exemplary embodiment, neural network 308 is an adaptive neural network that is adaptive to a changing environment in which the hearing system is used. In various embodiments, neural network 308 can be a time domain neural network (such as illustrated in FIG. 3) or a frequency domain neural network. The structure of neural network 308 can be highly flexible.

Figure 4:
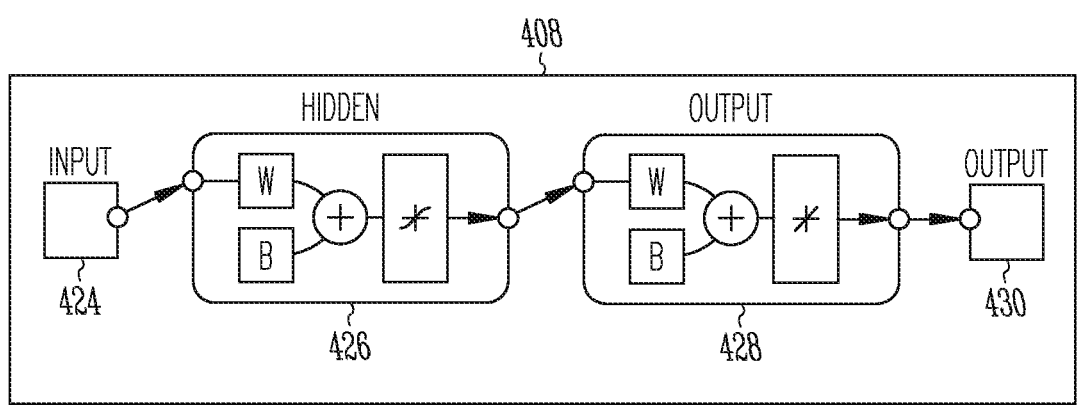
FIG. 4 is a block diagram illustrating an exemplary embodiment of the neural network of FIG. 1.
Figure 5:
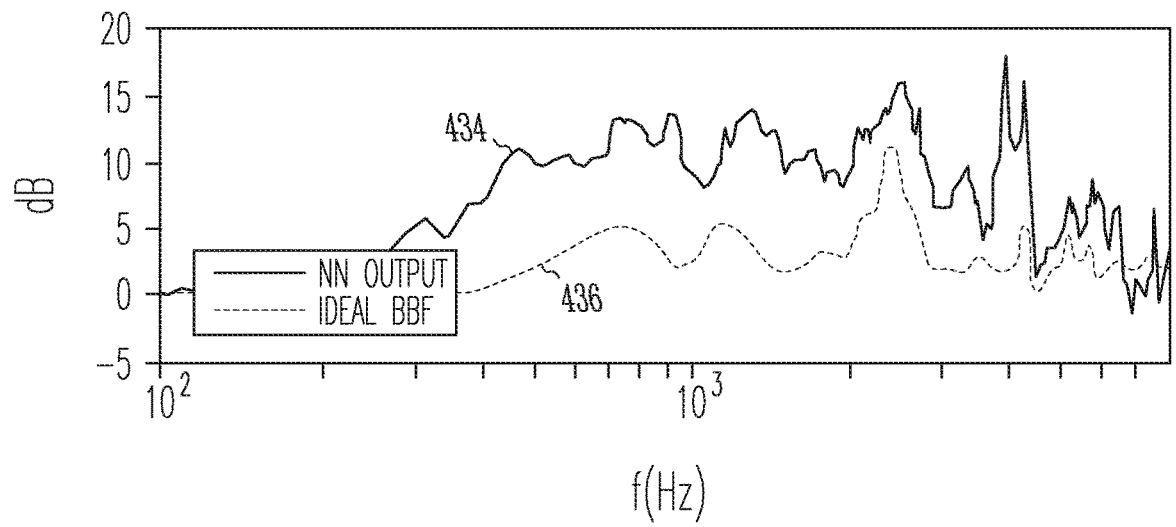
FIG. 5 is a graph illustrating performance of the exemplary neural network of FIG. 4 compared to performance of an exemplary ideal binaural beamformer.
Figure 6:
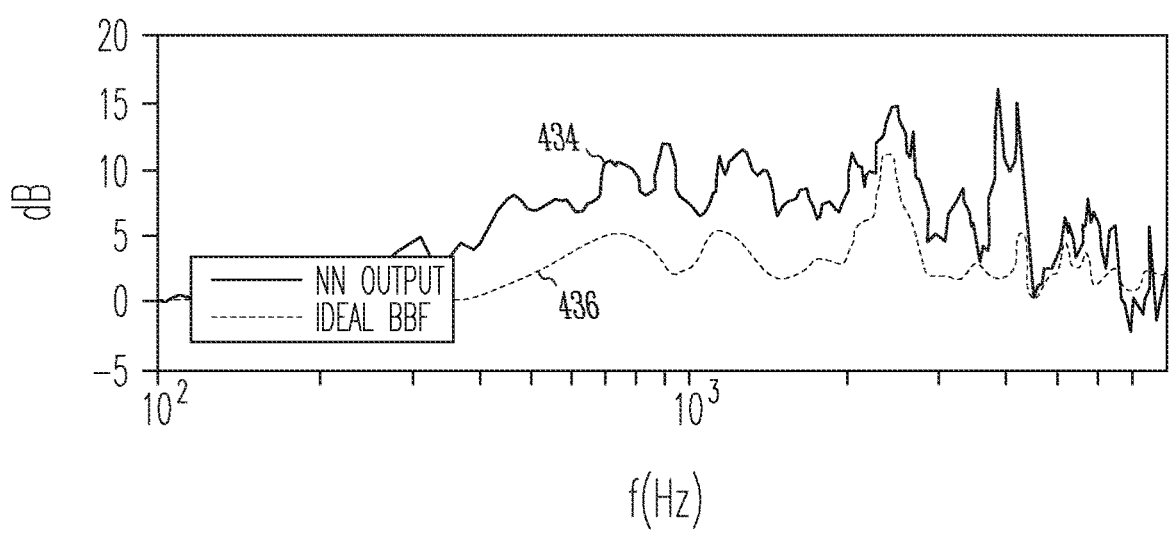
FIG. 6 is a graph illustrating performance of the exemplary neural network of FIG. 4 compared to performance of an exemplary ideal binaural beamformer.

FIG. 4 is a block diagram illustrating an exemplary embodiment of a neural network 408, which represent an exemplary embodiment of neural network 108. Neural network 408 includes an input 424, a nonlinear hidden layer 426, a linear output layer 428, and an output 430. In the illustrated embodiment, input 424 receives time sequence samples from microphones (such as from binaural microphones 202L and 202R, with 32 samples from each microphone). In various embodiments, neural network 408 can be trained on synthesized target sound (e.g., speech or music) in various types of noise conditions (e.g., with babble noise or machine noise) using various cost functions. Examples of the cost functions include mean squared error (MSE), weighted MSE, mean absolute error (MAE), statistical forecast error (SFE), and perceptual inspired metrics such as SII (speech intelligibility index) and STI (speech transmission index). In one experiment, for example, neural network 408 was trained on synthesized speech in babble noise conditions with the desired speech coming from front. During the training, the target signal was the clean speech and the MSE, a cost function, was minimized by properly adjusting synaptic weights in neural network 408, which included a plurality of synapses. After the training, the performance of neural network 408 in SNR improvement was tested on a separate training dataset and was compared to an ideal binaural beamformer (a linear binaural beamformer optimized for the testing condition). FIGS. 5 and 6 are each a graph illustrating performance of neural network 408 (NN OUTPUT) compared to performance of the ideal binaural beamformer (BBF). The graph plots an SNR 434 of neural network 408 and an SNR 436 of the ideal BBF over a range of frequencies, and shows the SNR improvement achieved by neural network 408. FIG. 5 shows the SNR improvement on an input signal having an average SNR of 5 dB. FIG. 6 shows the SNR improvement on an input signal having an average SNR of 0 dB.

The fact that neural network 408 can improve the SNR to an extent that exceeds the theoretical limit of linear binaural beamformer indicates that neural network 408 introduces nonlinearity to the signal. However, though a good SNR improvement was achieved, the distortion to the desired speech as well as the noise could be annoying. To reduce the audible distortion, sound quality measures can be incorporated into the cost function, the structure of the neural network can be adjusted, and/or the training data can be adjusted. The following is an example demonstrating a specific network structure (illustrated in FIG. 7) combined with carefully designed training data to achieve a balance between SNR improvement and distortion.

Figure 7:
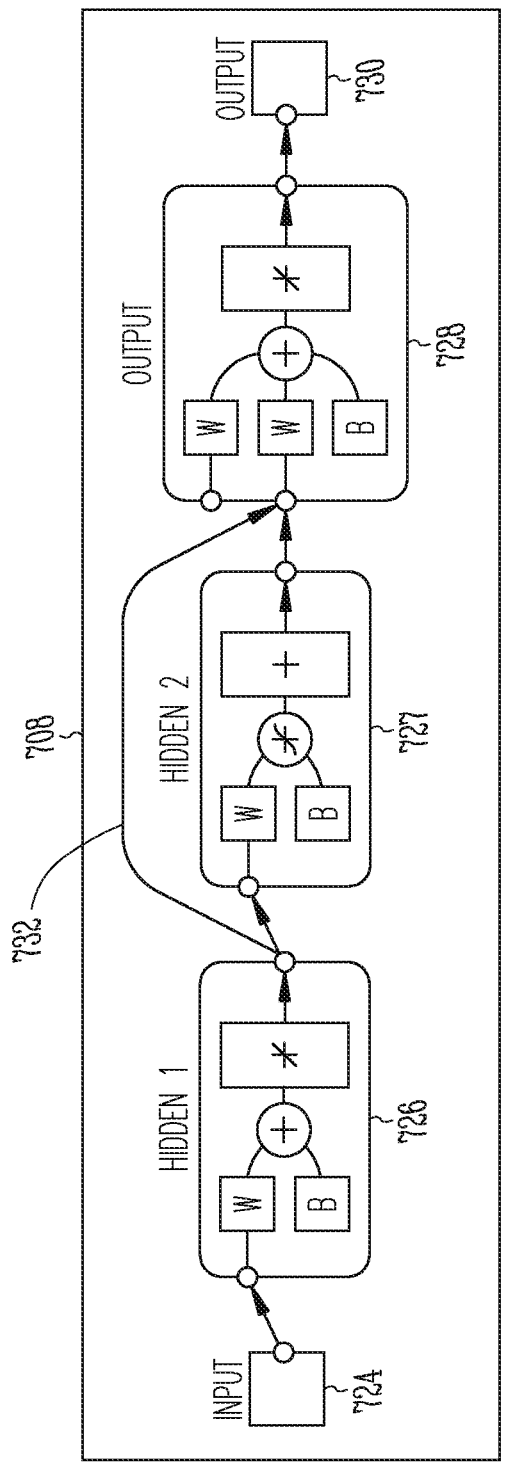
FIG. 7 is a block diagram illustrating another exemplary embodiment of the neural network of FIG. 1.

FIG. 7 is a block diagram illustrating an exemplary embodiment of a neural network 708, which represents another exemplary embodiment of neural network 108. Neural network 708 includes an input 724, a linear first hidden layer 726, a nonlinear second hidden layer 727, a linear output layer 728, and an output 730. In the illustrated embodiment, input 724 receives time sequence samples from microphones (such as from binaural microphones 202L and 202R, with 16 samples from each microphone). A shortcut connection 732 between the output of the linear first hidden layer 726 and the input of output layer 728 provides a direct path for a portion of the input signal to pass through without nonlinear distortion. Thus, neural network 708 includes a linear signal processing path between input 724 and output 730 and a nonlinear signal processing path between input 724 and output 730. The linear path includes first hidden layer 726 and output layer 728. The nonlinear path includes first hidden layer 726, second hidden layer 727, and output layer 728. In other words, first hidden layer 726 has an input directly connected to input 724 and an output. Second hidden layer 727 has an input directly connected to the output of hidden layer 726 and an output. Output layer 728 has an input directly connected to the output of hidden layer 726, another input directly connected to the output of hidden layer 727, and an output directly connected to output 730.

Figure 8:
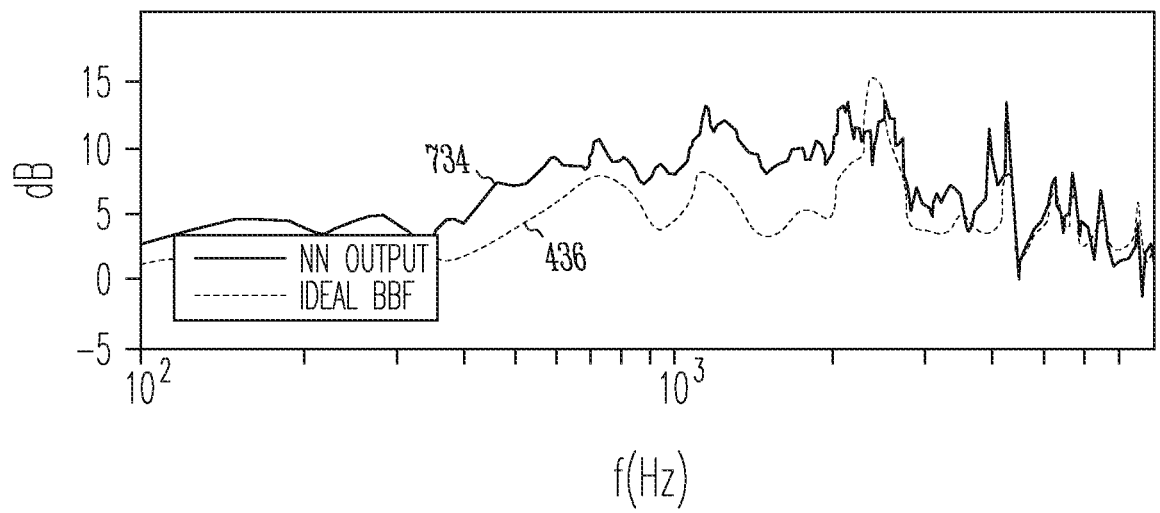
FIG. 8 is a graph illustrating performance of the exemplary neural network of FIG. 7 compared to performance of an exemplary ideal binaural beamformer.
Figure 9:
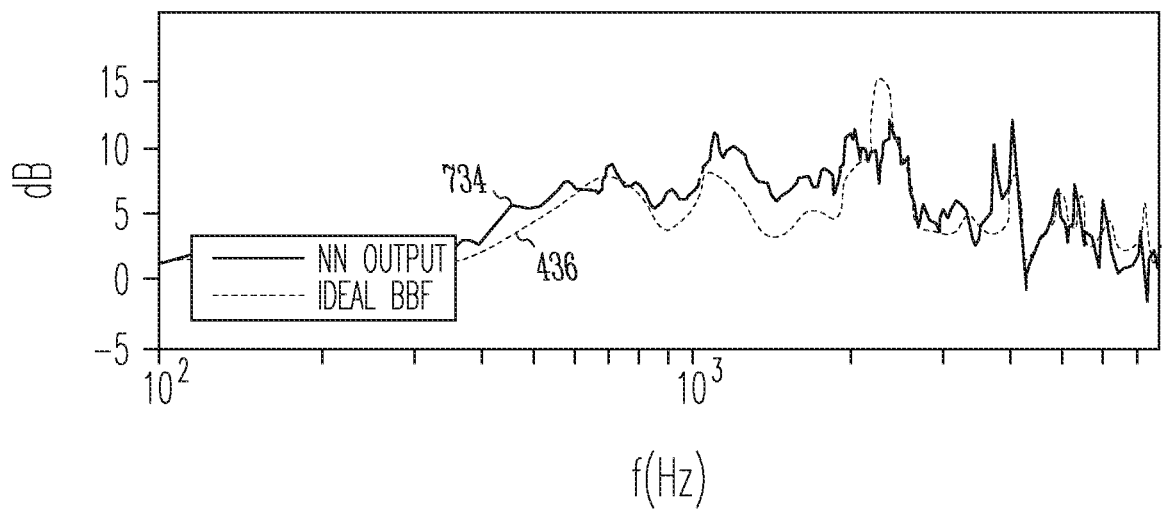
FIG. 9 is a graph illustrating performance of the exemplary neural network of FIG. 7 compared to performance of an exemplary ideal binaural beamformer.

Neural network 708 was trained at SNRs of 0 dB, 10 dB, and 20 dB with the target signal always being the clean speech. The training is also a crucial step for reducing distortion of the speech. FIGS. 8 and 9 are each a graph illustrating performance of neural network 708 (NN OUTPUT) compared to performance of the ideal binaural beamformer (BBF). The graph plots an SNR 734 of neural network 708 and SNR 436 of the ideal BBF over a range of frequencies, and shows the SNR improvement achieved by neural network 708. FIG. 8 shows the SNR improvement on an input signal having an average SNR of 5 dB. FIG. 9 shows the SNR improvement on an input signal having an average SNR of 0 dB. Compared to the example of neural network 408 as discussed above with reference to FIGS. 5-7, neural network 708 provided less SNR improvement (though still higher than the ideal BBF), but the distortion associated with neural network was virtually unperceivable.

Neural network 708 is illustrated in FIG. 7 and discussed above by way of example, but not by way of restriction. In various embodiments, neural network 108 can each include a linear signal processing path and a nonlinear signal processing path such that the output includes components being the input subjected to only linear signal processing and therefore not distorted as a result of nonlinear processing. For example, the nonlinear signal processing path can include one or more linear layers and one or more nonlinear layers, and the liner signal processing path can include only the one or more linear layers while bypassing each of the one or more nonlinear layers.

In various embodiments, the cost function in the training of neural network 108, including its various embodiments, can incorporate various speech intelligibility and sound quality measures to optimize the neural network for various working conditions and/or user preferences. In various embodiments, neural network 108, including its various embodiments, can be trained in both time domain and frequency domain. In various embodiments, neural network 108, including its various embodiments, can be fixed (i.e., kept unchanged after the training) or adaptive (i.e., dynamically adjustable based on the real environment). In various embodiments, neural network 108, including its various embodiments, can be implemented digitally, in the form of analog circuits, or as a combination of digital and analog circuits.

Figure 10:
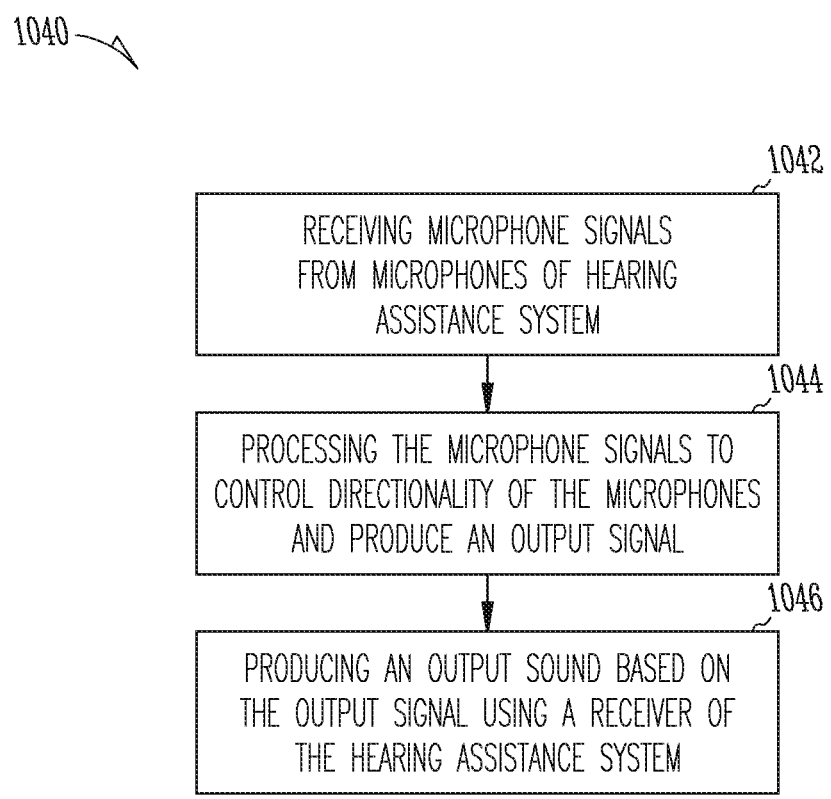
FIG. 10 is a flow chart illustrating an exemplary embodiment of a method for processing microphone signals using a neural network in a hearing system.

FIG. 10 is a flow chart illustrating an exemplary embodiment of a method 1040 for processing microphone signals using a neural network in a hearing system. Examples of the hearing system include system 100 and its various embodiments as described by this document. Examples for the neural network used in performing method 1040 include neural network 108 and its various embodiments as discussed in this document. In various embodiments, method 1040 can be performed to enhance a target sound in a noisy background for better listening to the target sound. In an exemplary embodiment, as discussed below as an example, the target sound is a speech, and method 1040 can be performed to improve intelligibility of speech in a noisy background.

At 1042, microphone signals are received from a plurality of microphones of the hearing system. The microphone signals include a speech received by the microphones. In an exemplary embodiment, the hearing system includes a pair of left and right hearing aids each being worn in or about an ear of a hearing aid wearer, such as the pair of left and right hearing aids 210L and 210R. The received microphone signals include a left microphone signal received from the left hearing aid and a right microphone signal received from the right hearing aid.

At 1044, the microphone signals are processed, using a neural network-based signal processing algorithm, to control a directionality of the plurality of microphones and produce an output signal. In various embodiments, the neural network-based signal processing algorithm can include a nonlinear signal processing algorithm. This includes, for example, processing the microphone signals using a linear signal processing path and a nonlinear signal processing path. In various embodiments, the microphone signals can be processed using a neural network trained for a desirable balance between an SNR and distortion of the speech. In an exemplary embodiment, the neural network is trained with a clean speech as the target signal and a mean squared error as a cost function. In an exemplary embodiment, the mean squared error is approximately minimized by adjusting synaptic weights in the neural network. In various embodiments, the microphone signals can be processed within a hearing device, such as a hearing aid, and/or one or more devices external to but communicatively coupled to the hearing aid. An example of such an external device include a cellphone. This allows for a distributed processing that off-loads the processing work from the hearing aid.

At 1046, an output sound is produced based on the output signal using a receiver (speaker) of the hearing assistance system. The output sound is delivered to the user of the hearing assistance system, such as a hearing aid wearer when the hearing assistance system includes the pair of left and right hearing aids.

In various embodiments, the present subject matter provides a neural network based binaural algorithm that can achieve performance exceeding the theoretical upper limit provided by a binaural beamformer in processing microphone signals. Neural network 408, as discussed above with reference to FIGS. 4-6, is an example that demonstrates that a substantially better SNR improvement can be achieved when compared to the upper limit of SNR improvement provided by a binaural beamformer. However, this is achieved at the cost of obvious nonlinear distortions to the target signal as well as the noise. If the distortion to the target signal is of concern, one could incorporate sound quality measures into the cost function during training of the neural network, adjust the structure of the neural network, and/or adjust training data. Neural network 708, as discussed above with reference to FIGS. 7-9, is an example that demonstrates a specific neural network structure that can achieve a balance between SNR improvement and distortion of the target signal when combined with carefully designed training data.

Hearing devices typically include at least one enclosure or housing, a microphone, hearing device electronics including processing electronics, and a speaker or "receiver." Hearing devices may include a power source, such as a battery. In various embodiments, the battery may be rechargeable. In various embodiments multiple energy sources may be employed. It is understood that in various embodiments the microphone is optional. It is understood that in various embodiments the receiver is optional. It is understood that variations in communications protocols, antenna configurations, and combinations of components may be employed without departing from the scope of the present subject matter. Antenna configurations may vary and may be included within an enclosure for the electronics or be external to an enclosure for the electronics. Thus, the examples set forth herein are intended to be demonstrative and not a limiting or exhaustive depiction of variations.

Its understood that digital hearing aids include a processor. For example, control circuit 104 and its various embodiments may be implemented in a processor. In digital hearing aids with a processor, programmable gains may be employed to adjust the hearing aid output to a wearer's particular hearing impairment. The processor may be a digital signal processor (DSP), microprocessor, microcontroller, other digital logic, or combinations thereof. The processing may be done by a single processor, or may be distributed over different devices. The processing of signals referenced in this application can be performed using the processor or over different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments the processor can be adapted to perform instructions stored in one or more memories, which may or may not be explicitly shown. Various types of memory may be used, including volatile and nonvolatile forms of memory. In various embodiments, the processor or other processing devices can execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

Various embodiments of the present subject matter support wireless communications with a hearing device. In various embodiments the wireless communications can include standard or nonstandard communications. Some examples of standard wireless communications include, but not limited to, Bluetooth™, low energy Bluetooth, IEEE 802.11 (wireless LANs), 802.15 (WPANs), and 802.16 (WiMAX). Cellular communications may include, but not limited to, CDMA, GSM, ZigBee, and ultra-wideband (UWB) technologies. In various embodiments, the communications are radio frequency communications. In various embodiments the communications are optical communications, such as infrared communications. In various embodiments, the communications are inductive communications. In various embodiments, the communications are ultrasound communications. Although embodiments of the present system may be demonstrated as radio communication systems, it is possible that other forms of wireless communications can be used. It is understood that past and present standards can be used. It is also contemplated that future versions of these standards and new fixture standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, ATM, Fibre-channel, Firewire or 1394, InfiniBand, or a native streaming interface. In various embodiments, such connections include all past and present link protocols. It is also contemplated that future versions of these protocols and new protocols may be employed without departing from the scope of the present subject matter.

In various embodiments, the present subject matter is used in hearing devices that are configured to communicate with mobile phones. In such embodiments, the hearing device may be operable to perform one or more of the following: answer incoming calls, hang up on calls, and/or provide two way telephone communications. In various embodiments, the present subject matter is used in hearing devices configured to communicate with packet-based devices. In various embodiments, the present subject matter includes hearing devices configured to communicate with streaming audio devices. In various embodiments, the present subject matter includes hearing devices configured to communicate with Wi-Fi devices. In various embodiments, the present subject matter includes hearing devices capable of being controlled by remote control devices.

It is further understood that different hearing devices may embody the present subject matter without departing from the scope of the present disclosure. The devices depicted in the figures are intended to demonstrate the subject matter, but not necessarily in a limited, exhaustive, or exclusive sense. It is also understood that the present subject matter can be used with a device designed for use in the right ear or the left ear, or both ears, of the wearer.

The present subject matter may be employed in hearing devices, such as headsets, hearing aids, speakers, cochlear implants, bone conduction devices, and personal listening devices.

The present subject matter is demonstrated for use in hearing devices, such as hearing aids, including but not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used in hearing assistance devices generally, such as cochlear implant type hearing devices. The present subject matter can also be used in deep insertion devices having a transducer, such as a receiver or microphone. The present subject matter can be used in devices whether such devices are standard or custom fit and whether they provide an open or an occlusive design. It is understood that other hearing devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method for transmitting a target sound to a listener, comprising:
    receiving microphone signals including the target sound from microphones;
    processing the microphone signals using a neural network to produce a processed signal including the target sound, the neural network including a linear signal processing path and a nonlinear signal processing path, the processing including using the nonlinear signal processing path to increase a signal-to-noise ratio (SNR) for the target sound and using the linear signal processing path to decrease distortion of the target sound;
    producing an output signal including the target sound using the processed signal; and
    producing an output sound based on the output signal using a speaker.

2. The method of claim 1, wherein processing the microphone signals using the neural network comprises processing the microphone signals to improve intelligibility of speech in a noisy background, the speech being the target sound.

3. The method of claim 1, further comprising training the neural network with a synthesized target sound in a noisy condition and a specified cost function.

4. The method of claim 3, wherein the target sound is speech, and training the neural network comprises training the neural network with a clean speech in a babble noise condition as the synthesized target sound in the noisy condition and a mean squared error as the cost function.

5. The method of claim 4; wherein training the neural network comprises approximately minimizing the mean squared error by adjusting synaptic weights of synapses of the neural network.

6. A method for transmitting a target sound to a listener, comprising:
   receiving microphone signals including the target sound from microphones;
   processing the microphone signals using a neural network to produce a processed signal including the target sound, the neural network including a linear signal processing path and a nonlinear signal processing path;
   producing an output signal including the target sound using the processed signal; and
   producing an output sound based on the output signal using a speaker,
   wherein receiving the microphone signals comprises receiving at least microphone signals from a pair of hearing devices worn by the listener.

7. The method of claim 6, wherein receiving the microphone signals further comprises receiving at least one microphone signal from a remote microphone that is external to the pair of hearing devices.

8. The method of claim 6, wherein processing the microphone signals using the neural network comprises processing the microphone signals using a processor of the pair of hearing devices.

9. The method of claim 6, wherein processing the microphone signals using the neural network comprises processing the microphone signals using a device that is external to the pair of hearing devices.

10. A hearing system for transmitting a target sound to a listener, comprising:
    microphones configured to receive input sounds including the target sound and to produce microphone signals using the input sounds;
    a control circuit configured to produce an output signal using a processed signal and including a neural network, the output signal including the target sound, the neural network including a linear signal processing path and a non-linear signal processing path, configured to produce the processed signal by processing the microphone signal through the linear and non-linear signal processing paths, and trained to process the microphone signals for a desirable balance between a signal-to-noise ratio (SNR) and distortion of the target sound; and
    a speaker configured to produce an output sound using the output signal.

11. The system of claim 10, comprising a pair of hearing devices configured to be worn by the listener and an external device configured to be communicatively coupled to the hearing devices, and wherein the microphones comprises a microphone placed in each of the hearing devices.

12. The system of claim 11, wherein the microphones comprise one or more remote microphones external to the hearing devices and configured to be communicatively coupled to the hearing devices.

13. The system of claim 11, wherein the hearing devices comprise the control circuit.

14. The system of claim 11, wherein the external device comprises the control circuit.

15. The system of claim 11, wherein the hearing devices and the external device each comprise a portion of the control circuit.

16. The system of claim 10, wherein the target sound is speech, and the neural network is configured to improve speech intelligibility.

17. The system of claim 16, wherein the neural network is configured to be adaptive to a changing environment in which the hearing system is used.

18. The system of claim 10, wherein the neural network comprises:
    a linear hidden layer configured to receive the microphone signals and to produce a linear output signal;
    a nonlinear hidden layer configured to receive the linear output signal and to produce a nonlinear output signal; and
    an output layer configured to receive the linear output signal and the nonlinear output signal and to produce the processed signal.

19. The method of claim 1, wherein receiving the microphone signals comprises receiving at least microphone signals from a pair of hearing devices worn by the listener, and processing the microphone signals using the neural network comprises processing the microphone signals using a device that is external to the pair of hearing devices.

20. The method of claim 19, wherein receiving the microphone signals further comprises receiving at least one microphone signal from a remote microphone that is external to the pair of hearing devices.

21. A hearing system for transmitting a target sound to a listener, comprising:
    a pair of hearing devices configured to be worn by the listener;
    an external device configured to be communicatively coupled to the hearing devices;
    microphones configured to receive input sounds including the target sound and to produce microphone signals using the input sounds, the microphones including a microphone placed in each of the hearing devices;
    a control circuit configured to produce an output signal using a processed signal and including a neural network, the output signal including the target sound, the neural network including a linear signal processing path and a non-linear signal processing path and configured to produce the processed signal by processing the microphone signal through the linear and non-linear signal processing paths; and
    a speaker configured to produce an output sound using the output signal.

22. The system of claim 21, wherein the microphones comprise one or more remote microphones external to the hearing devices and configured to be communicatively coupled to the hearing devices.

23. The system of claim 21, wherein the hearing devices comprise the control circuit.

24. The system of claim 21, wherein the external device includes the control circuit.

25. The system of claim 21, wherein the hearing devices and the external device each comprise a portion of the control circuit.

26. A hearing system for transmitting a target sound to a listener, comprising:
    microphones configured to receive input sounds including the target sound and to produce microphone signals using the input sounds;
    a control circuit configured to produce an output signal using a processed signal and including a neural network, the output signal including the target sound, the neural network including a linear signal processing path and a non-linear signal processing path and configured to produce the processed signal by processing the microphone signal through the linear and non-linear signal processing paths; and
    a speaker configured to produce an output sound using the output signal, wherein the neural network includes:
- a linear hidden layer configured to receive the microphone signals and to produce a linear output signal;
- a nonlinear hidden layer configured to receive the linear output signal and to produce a nonlinear output signal; and
- an output layer configured to receive the linear output signal and the nonlinear output signal and to produce the processed signal.

27. The system of claim 26, wherein the target sound is speech, and the neural network is configured to improve speech intelligibility.

* * * * *